United States Patent [19]

Smith

[11] Patent Number: 4,970,340

[45] Date of Patent: Nov. 13, 1990

[54] AMINE OXIDE PROCESS AND COMPOSITION

[75] Inventor: Kim R. Smith, Baton Rouge, La.

[73] Assignee: Ethyl Corporation, Richmond, Va.

[21] Appl. No.: 821,793

[22] Filed: Jan. 23, 1986

Related U.S. Application Data

[63] Continuation-in-part of Ser. No. 751,005, Jul. 1, 1985, Pat. No. 4,659,565.

[51] Int. Cl.$^5$ ............................................. C07C 291/00
[52] U.S. Cl. ......................................... 564/298; 424/70
[58] Field of Search ........................................ 564/298

[56] References Cited

U.S. PATENT DOCUMENTS

| | | | |
|---|---|---|---|
| 3,047,579 | 7/1962 | Witman | 564/297 X |
| 3,086,943 | 4/1963 | Lang | 564/297 X |
| 3,098,794 | 7/1963 | Dohr et al. | 564/297 X |
| 3,202,714 | 8/1965 | Zimmerer et al. | 564/297 |
| 3,215,741 | 11/1965 | Chadwick | 564/298 |
| 3,270,060 | 8/1966 | Wakeman et al. | 564/297 |
| 3,283,007 | 11/1966 | Chadwick | 564/298 |
| 3,333,000 | 7/1967 | Albert et al. | 564/298 |
| 3,432,555 | 3/1969 | Mahnken | 564/298 |
| 3,463,817 | 8/1969 | Mahnken | 564/298 |
| 3,471,562 | 10/1969 | Wakeman et al. | 564/297 X |
| 3,494,924 | 2/1970 | Bonetti et al. | 564/298 X |
| 3,525,772 | 8/1970 | Muratorio | 564/298 |
| 3,558,710 | 1/1971 | Stalioraitis et al. | 564/298 |
| 3,636,155 | 1/1972 | Muratorio | 564/298 |
| 3,657,251 | 4/1972 | Smetana | 564/297 X |
| 3,776,959 | 12/1973 | Stalioraitis | 564/298 |
| 4,206,195 | 7/1980 | Bolich, Jr. et al. | 424/16 |
| 4,247,480 | 1/1981 | Murata et al. | 564/298 |
| 4,421,740 | 12/1983 | Burton | 424/70 |
| 4,425,243 | 1/1984 | Green et al. | 564/298 X |
| 4,565,891 | 1/1986 | Correa et al. | 564/298 |

FOREIGN PATENT DOCUMENTS

| | | | |
|---|---|---|---|
| 704364 | 2/1965 | Canada | 564/298 |
| 1518104 | 5/1970 | Fed. Rep. of Germany | 564/298 |
| 1066763 | 4/1967 | United Kingdom | 564/298 |

OTHER PUBLICATIONS

Jungermann et al., "Soap and Chemical Specialties", Sep. 1964, pp. 59–62.
Hoh et al., J. Am. Chem. Soc. 40 (1963), pp. 268–271.
Kirk–Othmer, "Encyclopendia of Chemical Technology", 3rd Ed., p. 266.

*Primary Examiner*—Robert V. Hines
*Attorney, Agent, or Firm*—Joseph D. Odenweller

[57] ABSTRACT

A highly concentrated aqueous solution of a di–$C_{6-20}$ alkyl methylamine oxide containing at least 50 weight percent of the amine oxide can be made without gel formation by reacting at least 40 weight percent aqueous hydrogen peroxide with a di–$C_{6-20}$ alkyl methyl or ethylamine. These concentrated solutions offer large freight savings in shipping the amine oxides to remote locations.

17 Claims, No Drawings

AMINE OXIDE PROCESS AND COMPOSITION

This application is a continuation-in-part of application Ser. No. 751,005 filed July 1, 1985 and now U.S. Pat. No. 4,659,565.

BACKGROUND OF THE INVENTION

Trialkyl amine oxides can be made by reacting a trialkyl amine with aqueous hydrogen peroxide. They are useful for many purposes such as hair conditioners in shampoos as described in U.S. Pat. No. 3,086,943. When a $C_{10-16}$ alkyl dimethyl or ethyl alkyl amine oxide as described in U.S. Pat. No. 3,086,943 is made, the product will gel if the concentration of the amine oxide exceeds about 30 weight percent. This results in a fairly dilute aqueous tert-amine oxide solution. When such solutions are shipped to remote locations as they usually are, the freight charges will be fairly high because of the large amount of water that is being shipped.

Alkyl dimethylamine oxides are described in Kirk-Othmer "Encyclopedia of Chemical Technology", 3rd Ed. At page 266, Kirk-Othmer states that "when a strictly aqueous system is employed, final concentrations of amine oxide should be limited to below 35% since higher concentrations tend to gel and prevent good mixing."

Hoh et al., J. Am. Oil Chem. Soc., 40 (1963) page 268-271 describe the synthesis of dimethyl dodecylamine oxide by reaction of dimethyl dodecylamine with 35% aqueous hydrogen peroxide The product is a 30-40 weight percent aqueous solution of the amine oxide. Hoh et al. note that even using 35% aqueous hydrogen peroxide, the reaction mixture will gel unless diluted with water during the reaction Hoh et al. attempted to make dimethyl dodecylamine oxide without co-feeding water starting with 35%, 70% and 90% aqueous hydrogen peroxide. With 35% and 70% hydrogen peroxide, the product was a gel that could not be stirred. The reaction with 90% hydrogen peroxide was not completed because of darkening of the reaction mixture.

Chadwick U.S. Pat. No. 3,215,741 describes the preparation of di-$C_{1-2}$ alkyl $C_{10-20}$ alkyl amine oxides by reaction of the tert-amine with hydrogen peroxide While attempting to make the desirable concentrated solutions of the amine oxide, Chadwick found that when commercially available hydrogen peroxide containing 20-90 weight percent $H_2O_2$ was used, the reaction sets up to a gel resembling a thick starch paste long before completion of the reaction. Chadwick's solution to the problem was to co-feed at least 20% hydrogen peroxide and sufficient water to the tert-amine such that the final product was water diluted. When dimethyl dodecylamine was used the most concentrated amine oxide solution that could be obtained was only 30-40 weight percent amine oxide.

From the foregoing, it is apparent that a need exists for an amine oxide process that will give a highly concentrated solution of amine oxide without gel formation.

SUMMARY OF THE INVENTION

It has now been discovered that certain amine oxides can be prepared as an aqueous solution in concentrations of 50 weight percent amine oxide or higher. These amine oxides are di-$C_{6-20}$ alkyl methylamine oxides.

DESCRIPTION OF THE PREFERRED EMBODIMENTS

A preferred embodiment of the invention is a process for making a concentrated aqueous gel-free solution of a di-$C_{6-20}$ alkyl methylamine oxide, said process comprising reacting a di-$C_{6-20}$ alkyl methylamine with at least a stoichiometric amount of aqueous hydrogen peroxide containing initially at least 40 weight percent $H_2O_2$.

Previously known amine oxides having a higher alkyl substituent had only one such higher alkyl substituent such as stearyl dimethylamine oxide. These amine oxides cannot be made as aqueous solutions in concentrations containing over 40 weight percent active amine oxide because the solution will gel and cannot be adequately stirred. Suprisingly, it has now been found that when two of the alkyl groups are higher alkyl groups, the resulting amine oxide can form solutions containing in excess of 50 weight percent and up to 80 weight percent or more active amine oxide. From the gel encountered in making the known stearyl dimethylamine oxide at concentrations as low as 30 weight percent, it is very surprising that the otherwise similar amine oxide containing two higher alkyl groups remain fluid.

The prior art suggest that gel formation in the production of amine oxides can be avoided by using a dilute hydrogen peroxide (e.g. less than 20 weight percent $H_2O_2$) or by co-feeding water with the hydrogen peroxide to achieve the same dilution. It has now been surprisingly discovered that with the di-$C_{6-20}$ alkyl methylamines, gels are avoided not by using low concentrations of hydrogen peroxide or by co-feeding water but in sharp contrast, by using highly concentrated hydrogen peroxide of over 40 weight percent and preferably 50 weight percent $H_2O_2$ or higher.

The tert-amine oxides that can be made in highly concentrated aqueous solutions are those having the formula

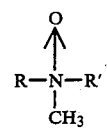

wherein R and R' are alkyl groups containing from 6 to about 20 carbon atoms. These alkyl groups are preferably linear but may have some branching not to exceed about two side branches. Some examples of the amine oxides are:
di-hexyl methylamine oxide
di-(2-ethylhexyl) methylamine oxide
hexyl dodecylmethylamine oxide
and the like.

One of the higher alkyl groups can contain as few as 4 carbon atoms if the other higher alkyl group contains 6 or more carbon atoms. Likewise the lower alkyl group can be either methyl or ethyl but is preferably methyl. Some further examples of the tertiary amines are:
di-hexyl methylamine
butyl hexyl methylamine
butyl octyl methylamine
dioctyl methylamine
octyl decyl methylamine
didecyl methylamine decyl dodecyl methylamine
didodecyl methylamine
octyl tetradecyl methylamine
hexyl hexadecyl methylamine
ditetradecyl methylamine
and the like including mixtures thereof.

In a more preferred embodiment, the longer alkyl groups contain 6 to 12 carbon atoms and the short alkyl group is methyl. These include:
dihexyl methylamine
diheptyl methylamine
dioctyl methylamine
dinonyl methylamine
didecyl methylamine
didodecyl methylamine
and the like.

In a still more preferred embodiment the $C_{6-12}$ alkyl groups are normal alkyl groups. Most preferably the higher alkyl groups are normal alkyl groups containing 8-10 carbon atoms or mixtures thereof, for example:
di-n-octyl methylamine
n-octyl n-decyl methylamine
di-n-decyl methylamine
and mixtures thereof.

It has been found to be critical to use hydrogen peroxide that is more concentrated than a commercial 35 weight percent aqueous hydrogen peroxide. For example, using 35% aqueous hydrogen peroxide with di-n-decyl methylamine leads to gel formation whereas use of 50 weight percent aqueous hydrogen peroxide forms a easily stirrable liquid product. Therefore, the preferred hydrogen peroxide solutions are at least 40 weight percent $H_2O_2$ and more preferably at least 50 weight percent $H_2O_2$. More concentrated hydrogen peroxide solutions can be used up to about 70 weight percent $H_2O_2$. The most preferred hydrogen peroxide concentration is about 50 weight percent $H_2O_2$.

The amount of aqueous hydrogen peroxide should be at least about a stoichiometric amount. For example at least about 0.9 moles and preferably 1.0 moles of hydrogen peroxide per mole of tert-amine. Good results can be achieved using about 1.1-1.3 mole parts of aqueous hydrogen peroxide per mole of tert-amine and more preferably about 1.15-1.25 mole parts of hydrogen peroxide per mole of tert-amine.

The reaction is conducted by adding the concentrated aqueous hydrogen peroxide to the stirred tert-amine. The reaction temperature can vary from below ambient to 100° C. or higher. A preferred reaction temperature is about ambient to 90° C. and most preferably about 60°-80° C.

Addition time will depend on temperature and scale. Preferably the hydrogen peroxide addition is not so rapid that a large accumulation of unreacted hydrogen peroxide occurs. Addition times in the range of 0.1-8 hours for small scale runs (on the order of 1 liter) up to 1-24 hours for large scale commercial operations are generally satisfactory.

Following the hydrogen peroxide addition, the reaction mixture can be stirred at reaction temperature for a period to be certain that the reaction has gone to completion. A ride time of about 1-12 hours is usually adequate. Following this, any unreacted hydrogen peroxide can be decomposed by adding a stoichiometric amount of a reducing agent such as $Na_2SO_3$.

The product is a concentrated aqueous easily stirrable solution of a di-$C_{6-20}$ alkyl $C_{1-2}$ alkyl amine oxide or in the more preferred case a solution of a di-$C_{6-12}$ methylamine oxide. The solution contains at least 50 weight percent amine oxide, preferably at least 60 weight percent amine oxide and most preferably at least 70 weight percent amine oxide and are still mobile liquids. For example, the reaction of di-n-decyl methylamine with 50 weight percent aqueous hydrogen peroxide yielded an aqueous solution of 79 weight percent di-n-decyl methylamine oxide and was an easily stirrable liquid.

The following examples serve to show how the process is conducted and the properties of the resulting amine oxide solutions.

EXAMPLE 1

In a reaction vessel was placed 176.0 grams (0.56 moles) of didecyl methylamine and 1.1 grams diethylenetriamine pentaacetic acid (DTPA). This was stirred at 65° C. while 48.0 grams (0.67 moles) of 50 weight percent aqueous hydrogen peroxide was added dropwise over a 1 hour period. Temperature was raised to 75° C. and the mixture stirred at 75° C. for 7 hours under nitrogen. The product was analyzed by wet chemical methods and determined 79 weight percent didecyl methylamine oxide. Unreacted amine was below the level of detection.

EXAMPLE 2

In a reaction vessel was placed 284.3 grams (1.0 mole) of a mixture of di-alkyl methylamine consisting essentially of 25 weight percent dioctyl methylamine, 25 weight percent didecyl methylamine and 50 weight percent octyldecyl methylamine and 1.4 grams diethylenetriamine pentaacetic acid (DTPA). This was stirred at 65° C. and then 83.5 grams (1.2 moles) of 50 weight percent aqueous hydrogen peroxide was added dropwise over a 1 hour period followed by a 7 hour ride at 75° C. The product was analyzed by wet chemical methods and determined to be 78.6 weight percent dialkyl methylamine oxide in which the alkyls were n-decyl and n-octyl. Unreacted amine was undetectable.

EXAMPLE 3

In a reaction vessel was placed 288.4 grams (1.17 moles) of di-n-octyl methylamine and 1.4 grams DTPA. This was stirred at 65° C. while 95.5 grams (1.4 moles) of 50 weight percent aqueous hydrogen peroxide was added dropwise over a 1 hour period. Temperature raised to 75° C. The product was analyzed by wet chemical methods and determined to be 79 weight percent di-n-octyl methylamine oxide and 0.1 weight percent free tert-amine.

EXAMPLE 4 Comparative Example

This experiment was similar to Example 3 except that 35 weight percent aqueous hydrogen peroxide was used.

In a reaction vessel was placed 216.6 grams (0.69 moles) of di-n-decyl methylamine oxide and 1.4 grams of DTPA. While stirring at 65° C., addition of 81.0 grams (0.83 moles) of 35 weight percent aqueous hydrogen peroxide was added over a 1 hour period. The temperature was raised to 75° C. and stirring continued. In a short period the mixture gelled and could not be stirred until isopropanol diluent was added.

As the above results show, in sharp contrast with what is reported for the conversion of higher alkyl dimethylamine to their oxides, the di-higher alkyl methylamines can be converted to their amine oxides without gelling by using a more concentrated aqueous hydrogen peroxide rather than by dilution with water.

The di-higher alkyl methylamine oxides made by the present process are useful in detergent compositions and especially in hair shampoo and hair conditioner.

I claim:

1. A process for making a concentrated aqueous gel-free solution of a di-$C_{6-12}$ alkyl methylamine oxide containing 50–80 weight percent of said di-$C_{6-12}$ alkyl methylamine oxide, said process consisting essentially of reacting a di-$C_{6-12}$ alkyl methylamine with at least a stoichiometric amount of aqueous hydrogen peroxide containing initially at least 40 weight percent $H_2O_2$.

2. A process of claim 1 wherein said aqueous hydrogen peroxide is about 50 weight percent $H_2O_2$.

3. A process of claim 1 wherein said di-$C_{6-12}$ alkyl methylamine is dioctylmethylamine.

4. A process of claim 3 wherein said aqueous hydrogen peroxide is about 50 weight percent $H_2O_2$.

5. A process of claim 1 wherein said di-$C_{6-12}$ alkyl methylamine is didecylmethylamine.

6. A process of claim 5 wherein said aqueous hydrogen peroxide is about 50 weight percent $H_2O_2$.

7. A process of claim 1 wherein said di-$C_{6-12}$ alkyl methylamine is didodecylmethylamine.

8. A process of claim 7 wherein said aqueous hydrogen peroxide is about 50 weight percent $H_2O_2$.

9. A gel-free aqueous solution of a tert-amine oxide, said solution consisting essentially of less than 50 weight percent water and at least 50 weight percent of a di-$C_{6-12}$ alkyl methylamine oxide.

10. An aqueous solution of claim 9 wherein said di-$C_{6-12}$ alkyl methylamine oxide is di-$C_8$–$C_{10}$ alkyl methylamine oxide.

11. An aqueous solution of claim 9 consisting essentially of less than 40 weight percent water and at least 60 weight percent of said di-$C_{6-12}$ alkyl methylamine oxide.

12. An aqueous solution of claim 11 wherein said di-$C_{6-12}$ alkyl methylamine oxide is a di-$C_{8-10}$ alkyl methylamine oxide.

13. An aqueous solution of claim 9 consisting essentially of less than 30 weight percent water and at least 70 weight percent of said di-$C_{6-12}$ alkyl methylamine oxide.

14. An aqueous solution of claim 13 wherein said di-$C_{6-12}$ alkyl methylamine oxide is a di-$C_{8-10}$ alkyl methylamine oxide.

15. An aqueous solution of claim 14 wherein said di-$C_{8-10}$ alkyl methylamine oxide is di-n-octyl methylamine oxide.

16. An aqueous solution of claim 14 wherein said di-$C_{8-10}$ alkyl methylamine oxide is di-n-decyl methylamine oxide.

17. An aqueous solution of claim 14 wherein said di-$C_{8-10}$ alkyl methylamine oxide is a mixture of di-alkyl methylamine oxides in which the alkyl groups are both n-octyl and n-decyl.

* * * * *